(12) United States Patent
Hamada et al.

(10) Patent No.: US 8,822,186 B2
(45) Date of Patent: Sep. 2, 2014

(54) METHOD FOR PRODUCING MICROBIAL FERMENTATION PRODUCT

(75) Inventors: Saki Hamada, Kamisu (JP); Shingo Koyama, Kamisu (JP); Kazuhiro Onozuka, Kamisu (JP); Takaaki Watanabe, Kamisu (JP)

(73) Assignee: Kao Corporation, Tokyo (JP)

( * ) Notice: Subject to any disclaimer, the term of this patent is extended or adjusted under 35 U.S.C. 154(b) by 135 days.

(21) Appl. No.: 13/389,422

(22) PCT Filed: Aug. 20, 2010

(86) PCT No.: PCT/JP2010/005153
§ 371 (c)(1),
(2), (4) Date: Feb. 7, 2012

(87) PCT Pub. No.: WO2011/024422
PCT Pub. Date: Mar. 3, 2011

(65) Prior Publication Data
US 2012/0135484 A1    May 31, 2012

(30) Foreign Application Priority Data

Aug. 25, 2009  (JP) ................. 2009-193954

(51) Int. Cl.
*C12P 7/22*  (2006.01)
(52) U.S. Cl.
CPC ........................ *C12P 7/22* (2013.01)
USPC ........................................ 435/155
(58) Field of Classification Search
CPC ....................................... C12P 7/02
USPC ....................................... 435/155
See application file for complete search history.

(56) References Cited

U.S. PATENT DOCUMENTS

| 4,798,799 | A | 1/1989 | Farbood et al. |
| 4,970,163 | A | 11/1990 | Farbood et al. |
| 2010/0028964 | A1* | 2/2010 | Hama et al. ............. 435/155 |
| 2010/0233766 | A1* | 9/2010 | Igarashi et al. ............ 435/126 |

FOREIGN PATENT DOCUMENTS

| CN | 1683352 A | 10/2005 |
| EP | 0 419 026 A1 | 3/1991 |
| EP | 1 997 879 A1 | 12/2008 |
| EP | 2 400 025 A1 | 12/2011 |
| JP | 62-074281 A | 4/1987 |
| JP | 3-224478 A | 10/1991 |
| JP | 2008-212087 A | 9/2008 |
| JP | 2009-183146 A | 8/2009 |
| WO | WO 2007/097106 A1 | 8/2007 |
| WO | WO 2008/108101 A1 | 9/2008 |

OTHER PUBLICATIONS

International Search Report, PCT/JP2010/005153, Sep. 21, 2010.
International Preliminary Report on Patentability and Translation of the Written Opinion of the International Searching Authority, dated for Mar. 22, 2012, for corresponding International Application No. PCT/JP2010/005153.
Supplementary European Search Report for corresponding European Patent Application No. 108114181.0, dated Jan. 3, 2013.

* cited by examiner

*Primary Examiner* — Tekchand Saidha
*Assistant Examiner* — Md. Younus Meah
(74) *Attorney, Agent, or Firm* — Birch, Stewart, Kolasch & Birch, LLP

(57) ABSTRACT

Disclosed is a method for producing 1-(2-hydroxyethyl)-2,5,5,8a-tetramethyldecahydronaphthalene-2-ol represented by formula (2),

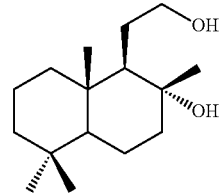

(2)

wherein microbial conversion is carried out using a compound(s) represented by formula (1a) and/or (1b) as a substrate,

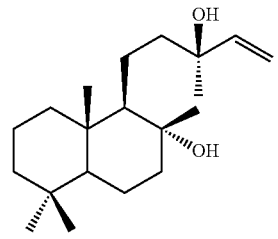

(1a)

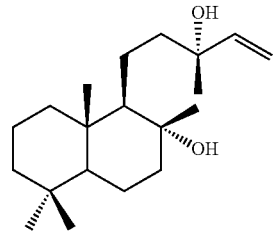

(1b)

the resulting culture product, in which microorganisms obtained by the microbial conversion are contained, and a solvent having an SP value within the range of 7.5 to 9.0 [(cal/cm$^3$)$^{1/2}$] are mixed together, and subsequently the aqueous phase is removed therefrom.

4 Claims, No Drawings

METHOD FOR PRODUCING MICROBIAL FERMENTATION PRODUCT

FIELD OF THE INVENTION

The present invention relates to a method for producing 1-(2-hydroxyethyl)-2,5,5,8a-tetramethyldecahydronaphthalene-2-ol useful as an intermediate for the production of 3a,6,6,9a-tetramethyldodecahydronaphtho[2,1-b]furan.

BACKGROUND OF THE INVENTION 3a,6,6,9a-Tetramethyldodecahydronaphtho[2,1-b]furan (hereinafter, indicated as "compound A") is a fragrance component that is contained in ambergris, a pathological secretion produced in the body of sperm whale, and is an important compound indispensable as an amber-based fragrance. Compound A is produced by a chemical synthesis method using sclareol, which is extracted mainly from clary sage (*Salvia sclarea* L.), as a starting material. As an intermediate of compound A, 3a,6,6,9a-tetramethyldecahydronaphtho[2,1-b]furan-2(1H)-one (hereinafter, indicated as "sclareolide") and 1-(2-hydroxyethyl)-2,5,5,8a-tetramethyldecahydronaphthalene-2-ol (hereinafter, indicated as "diol") are known.

However, the chemical synthesis method described above has a problem that the environmental burden is heavy, and the yield or the purity cannot be obtained at sufficient level.

Meanwhile, there have been reported methods for producing the compound A by obtaining an intermediate of the compound A from sclareol by microbial conversion and cyclizing the intermediate (for example, Patent Documents 1 and 2).

Specifically, in the Patent Documents 1 and 2, separation and purification of the diol obtained by microbial conversion are carried out by subjecting a culture fluid to solvent extraction using ethyl acetate, subsequently drying the extract, dissolving the resultant extract in warm hexane/ethyl acetate or hexane/chloroform, and crystallizing the diol from the solution.

However, since unreacted sclareol or sclareolide, microorganisms, culture medium components, and the like are mixedly present in a culture fluid obtained by microbial conversion of sclareol, separation and purification of the diol only is very difficult to achieve by the solvent extraction method using ethyl acetate.

As such, there has been reported a method of filtering a culture fluid using a filter having a mesh size of a specific range to separate the bacterial cells, subsequently dissolving the residues on the filter with ethanol, filtering the solution again, and the like to recover the diol with high purity (Patent Document 3).

PRIOR ART DOCUMENTS

Patent Document

Patent Document 1: JP-A No. 3-224478
Patent Document 2: JP-A No. 62-74281
Patent Document 3: JP-A No. 2008-212087

SUMMARY OF THE INVENTION

The present invention provides a method for producing 1-(2-hydroxyethyl)-2,5,5,8a-tetramethyldecahydronaphthalene-2-ol represented by the formula (2),

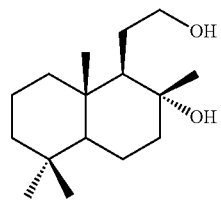

(2)

wherein microbial conversion is carried out using a compound(s) represented by the following formula (1a) and/or (1b) as a substrate,

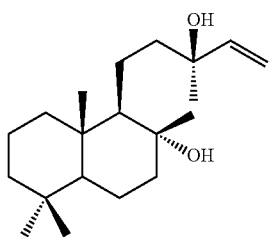

(1a)

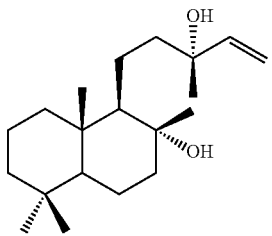

(1b)

the resulting culture product, in which microorganisms obtained by the microbial conversion are contained, and a solvent having an SP value within the range of 7.5 to 9.0 $[(cal/cm^3)^{1/2}]$ are mixed together, and subsequently the aqueous phase is removed therefrom.

MODES FOR CARRYING OUT THE INVENTION

Crystallized diol obtained by solvent extraction method using ethyl acetate as described above has low diol purity and strong abnormal odor with yellowish color. In particular, it is found that the culture odor originating from microorganisms is strong, and even when the diol is obtained by crystallization, further purification is necessary to lower the abnormal odor and to improve the color, resulting that the production process is very complicated. Presence of strong culture odor originating from microorganisms in the diol obtained is a big problem considering that the diol is to be used as a raw fragrance material.

Meanwhile, the method of separating bacterial cells using a filter and subsequently dissolving them in ethanol followed by filtering also has a complicated production process as it requires two filtering operations.

Under the circumstances, the present invention relates to a method capable of producing diol with favorable color and low abnormal odor strength efficiently with fewer purification processes.

The inventors of the present invention conducted intensive studies regarding a method for producing diol, and as a result, they found that, when a culture product obtained by microbial conversion is mixed with a solvent having an SP value within the range of 7.5 to 9.0 [(cal/cm$^3$)$^{1/2}$], diol with favorable color and reduced abnormal odor, in particular the culture odor, can be recovered, because the impurities originating from microorganisms are not extracted. Further, they also found that, although mixing the culture product with ethanol does not result in separation into a solvent phase and an aqueous phase so that the diol cannot be extracted with ethanol, use of a solvent having an SP value within the range of 7.5 to 9.0 [(cal/cm$^3$)$^{1/2}$] is capable of dissolving the diol in the solvent and directly extracting the diol, and thus the diol can be recovered with high yield from the culture product only with a single separation process.

According to the present invention, a high quality diol with favorable color and low abnormal odor can be produced efficiently with fewer purification processes.

In the present invention, the microorganisms that can be utilized in the microbial conversion are not particularly limited as long as they are microorganisms having an ability to produce the diol, which is an intermediate of the compound A, by using the compound(s) represented by the formula (1a) and/or formula (1b) as a substrate, and to release the diol outside of the bacterial cells. For example, microorganisms belonging to the class *Ascomycetes*, microorganisms belonging to the genus *Cryptococcus*, microorganisms belonging to the class *Basidiomycetes*, microorganisms belonging to the genus *Hyphozyma*, and the like may be mentioned. Among these, microorganisms belonging to the class *Ascomycetes* and microorganisms belonging to the genus *Hyphozyma* are preferred, from the viewpoint of the production efficiency for the diol, which is an intermediate of the compound A. An example of the microorganisms belonging to the class *Ascomycetes* may include microorganisms designated as *Ascomycete* sp. KSM-JL2842 and deposited with the International Patent Organism Depositary at the National Institute of Advanced Industrial Science and Technology (address: Tsukuba Central 6, 1-1-1, Higashi, Tsukuba-shi, Ibaraki-ken) on Jan. 12, 2006, under the Accession No. FERM P-20759. An example of the microorganisms belonging to the genus *Hyphozyma* may include the strain ATCC20624 described in Japanese Patent No. 2547713.

The microorganisms that can be utilized in the microbial conversion can be isolated from soil by evaluating the ability of microorganisms to produce the diol, which is an intermediate of the compound A, as an indicator. The ability to produce the diol, which is an intermediate of the compound A, can be evaluated by culturing test microorganisms in a culture medium containing the compound(s) represented by the formula (1a) and/or (1b), and detecting the diol, which is an intermediate of the compound A, contained in the culture medium. Detection of the diol, which is an intermediate of the compound A, can be carried out using conventionally known analysis methods such as gas chromatography (GC), gas-liquid chromatography (GLC), thin layer chromatography (TLC), high performance liquid chromatography (HPLC), infrared spectroscopy (IR), and nuclear magnetic resonance (NMR).

There are no particular limitations imposed on the culture conditions upon the microbial conversion, and a medium of any composition can be used as long as the medium contains the compound(s) represented by the formula (1a) and/or (1b) and enables growth of the microorganisms. Examples of media that can be used include solid media, fluid media, and the like, which contain carbon sources such as monosaccharides, disaccharides, oligosaccharides, polysaccharides, and organic acid salts; nitrogen sources such as inorganic and organic ammonium salts, nitrogen-containing organic substances, and amino acids; metallic minerals such as sodium chloride, ferrous sulfate, magnesium sulfate, manganese sulfate, zinc sulfate, and calcium carbonate; vitamins; and the like. Furthermore, the medium may also contain a surfactant or a defoaming agent in accordance with the culture conditions and the like.

There are no particular limitations imposed on the optimum pH range and the optimum temperature in terms of the culture conditions. For example, the optimum pH range is pH 3 to 8, preferably pH 4 to 8, and more preferably pH 5 to 7, and the optimum temperature of the fluid is 10 to 35° C., preferably 15 to 30° C., and more preferably 20 to 30° C. The duration of culture is not particularly limited, and, for example, is 1 to 10 days from the addition of the substrate. Culture can be carried out by shaking culture, aerobic culture, agitated culture, anaerobic culture, static culture and culture using a fermentation bed, as well as a resting cell reaction and an immobilized cell reaction.

The concentration of the compound(s) represented by the formula (1a) and/or (1b) that is added to the medium as a substrate, is preferably set to 0.1 to 50% by weight (hereinafter, simply described as "%") in the medium, from the viewpoint of the production efficiency for the diol, which is an intermediate of the compound A. The substrate may be added to the medium prior to the culture, or may be added in the middle of the culture.

In the culture product obtained by microbial conversion, microorganisms that are used for the microbial conversion are mixedly present in addition to the diol represented by the formula (2). However, the culture product itself containing the microorganisms is used for the present invention. Further, in the culture product, impurities such as unreacted sclareol, sclareolide, and medium components may be included.

Before the culture product in which the microorganisms are contained is mixed with a solvent having an SP value within the range of 7.5 to 9.0 [ (cal/cm$^3$)$^{1/2}$], (herein below, the unit is omitted), from the viewpoints of suppressing the incorporation of impurities that are present inside the bacterial cells into the solvent, and ameliorating the odor and color of the diol thus produced, it is preferable that the microorganisms are not subjected to a physical treatment such as crushing or grinding, a chemical treatment such as a surfactant treatment, a biochemical treatment such as a lytic enzyme, or the like mix.

Further, from the viewpoint of ameliorating the odor and color of the diol to be produced, it is preferable to remove a part of water such as medium components in the culture product by centrifugation or the like in advance, before the culture product in which the microorganisms are contained is mixed with a solvent having an SP value within the range of 7.5 to 9.0.

Centrifugation is carried out using a general centrifuge such as a separation plate type centrifuge, a cylinder type centrifuge or a decanter type centrifuge, and also any one of batch type and continuous type may be used. For the conditions of centrifugation, the temperature is preferably 5 to 60° C. The centrifugal force may be appropriately determined depending on the amount of solid matter contained in a culture product. It is preferably 500 to 20000 G, more preferably 1000 to 10000 G. The treatment time may be appropriately determined depending on acceleration speed. It is preferably 1 to 60 minutes, and more preferably 2 to 30 minutes. The number of rotation adopted for centrifugation is, in the case of a cylinder type centrifuge, preferably 2000 to 12000 r/min, more preferably 3000 to 12000 r/min, and even more preferably 7000 to 12000 r/min.

The water content in the culture product from which a part of water is removed (herein below, also referred to as "precipitate") is preferably 80% by weight or less, more preferably 70% by weight or less, and even more preferably 60% by weight or less.

Examples of the solvent having an SP value within the range of 7.5 to 9.0, which is mixed with the culture product in which the microorganisms are contained, include cyclohexane (SP value of 8.2), 4-methyl-2-pentanone (SP value of 8.4), xylene (SP value of 8.8), toluene (SP value of 8.9), and the like. It may be used either singly or in combination of two or more kinds.

Further, a solvent obtained by appropriately combining a solvent having the SP value outside the range of 7.5 to 9.0 such that the SP value of the solvent mixed is within the range and by preparing the combined solvent to have the SP value within the range may also be used. By using a solvent having the SP value within the range of 7.5 to 9.0, time required for diol extraction can be shortened and also the use amount of the solvent for extraction can be reduced, and therefore work efficiency is improved.

As used herein, the SP value represents the solubility parameter, and SP values are described in, for example, "Fundamentals and Applications of SP Values and Calculation Methods" (Johokiko Co., Ltd., 2005), Polymer Handbook Third Edition (A Wiley-Interscience Publication, 1989), and the like. Furthermore, for the solvents of which specific values of the SP value are not described in the foregoing documents, the SP values can be determined by using the Fedors method described in, for example, "Fundamentals and Applications of SP Values and Calculation Methods" as mentioned above, Polymer Engineering and Science, Vol. 14, No. 2, 147-154 (1974), and the like. In the case of using plural solvents in combination, the SP value is determined by calculating a volume average value of the SP values of the respective solvents.

From the viewpoints of improving recovery ratio (yield) or purity of the diol and obtaining favorable odor and color, it is preferable to use a solvent with an SP value of 8.0 to 9.0, with being more preferable of an SP value of 8.2 to 9.0, even more preferable of an SP value of 8.5 to 9.0, and even more preferable of an SP value of 8.5 to 8.9.

According to the present invention, it is preferable to set the use amount of the solvent appropriately in accordance with the solvent used. However, from the viewpoints of the solubility of the diol, the amelioration of the odor and color of the diol produced, and the recovery ratio (yield) of the diol, the use amount of the solvent based on 100 mL of the culture fluid is preferably 10 to 1000 mL, and more preferably 10 to 100 mL. In particular, the use amount of the solvent based on 1 g of the diol present in the culture fluid is preferably 1 to 1000 mL, and more preferably 10 to 100 mL.

The temperature of the mixture fluid obtainable after mixing the culture product with the solvent is preferably 0 to 80° C., and more preferably 20 to 65° C. At this time, the mixing time is preferably 1 to 120 minutes, and more preferably 5 to 60 minutes from the viewpoints of the solubility of the dial and ameliorating the odor and color of the diol to be produced.

Subsequently, the mixture fluid is separated into a solvent phase and an aqueous phase and the aqueous phase is removed. As microorganisms, impurities originating from the microorganisms and the like are contained in an aqueous phase, the impurities and the like can be removed by this process. Further, the culture odor can be also reduced. As a means for separation into a solvent phase and an aqueous phase, there are static separation, centrifugal separation, and the like.

It is preferable that the static separation is carried out for 10 to 60 minutes and the solvent phase is collected. The temperature for static separation is not specifically limited. However, it is preferably 0 to 80° C., and more preferably 20 to 65° C.

Further, for centrifugation, the conditions described above can be adopted. However, the conditions can be suitably adjusted depending on separation state.

The solvent phase obtained after removal of an aqueous phase may be subjected to further filtration, as required, from the viewpoint of removing any floating matters contained in the solvent phase. Filtration is carried out using a general method such as suction filtration, pressure filtration, centrifugal filtration, or natural filtration. Among these methods, suction filtration is preferred. The mesh size of the filter used in the filtration is preferably 0.1 to 10 μm, and more preferably 0.2 to 1 μm, from the viewpoints of the recovery ratio of the diol and an improvement of purity. The material of the filter is not particularly limited, if it is resistant to a solvent. Specific examples thereof include filters made of resins such as polypropylene, polyester, or nylon; filters made of ceramics, filters made of metals, and the like.

By subjecting the solvent phase or the filtrate obtained accordingly to drying and/or crystallization, which is commonly carried out during a purification process, the dial can be obtained with high yield. As the diol obtained according to the method of the present invention has favorable color and reduced culture odor originating from microorganisms, a purification process for improving color and reducing abnormal odor can be simplified. The form of the diol may be any of powder form, solid form, liquid form and the like.

When drying is carried out during a purification process, there are no particular limitations on the method of drying. The temperature for drying is preferably from room temperature to 90° C. Further, drying under reduced pressure can be also carried out.

When crystallization is carried out during a purification process, there are no particular limitations on the method of crystallization. For example, there is a method of subjecting the solvent phase or the filtrate as described above to an impurity removal operation such as activated carbon filtration or fine filtration as necessary, and after that precipitating crystals of the diol through cooling, concentration, addition of a poor solvent or the like. Examples of the organic solvent used in crystallization include methanol, ethanol, isopropanol, acetone, tetrahydrofuran, ethyl acetate, acetonitrile, and the like. Among these, methanol, ethanol and isopropanol are preferred, while ethanol is even more preferred. These organic solvents may be used either singly or a combination of two or more kinds may be used as a mixture.

In the case of adding a poor solvent, it is preferable to use hexane or water.

According to the present invention, from the viewpoint of production efficiency, the recovery ratio (yield) of the diol obtained after the drying, crystallization, and/or the like is preferably 60% or greater, more preferably 65% or greater, even more preferably 70% or greater, and even more preferably 80% or greater.

Further, the diol thus obtained according to the method of the present invention can be converted to the compound A through cyclodehydration in various solvents, using an acidic catalyst, for example, p-toluene sulfonic acid, p-toluene sulfonic acid chloride, a catalytic amount of sulfuric acid, an acidic ion exchanger, or the like.

EXAMPLES

[Microbial Conversion]

One platinum loop of *Ascomycete* sp. KSM-JL2842 (FERM P-20759) was inoculated into 2.1% YM broth, and subjected to shaking culture at 25° C. for three days. The resultant was used as an inoculum. Subsequently, the 0.3% of inoculum was inoculated into a medium containing 2.1% YM broth and 0.1% magnesium sulfate, and aerated and agitated culture was carried out in a 30-L fermenter at a fluid temperature of 24° C., an amount of air aeration of 0.5 vvm, and a stirring speed of 200 r/min for three days. Thereafter, a substrate including 10% Tween 80 (registered trade mark) and 20% sclareol was added to the culture to obtain a sclareol concentration in the culture fluid of 5%. For 4 days from the addition of the substrate, aerated and agitated culture was performed while the pH was adjusted to 6.0 using 1 N NaOH and 1 N HCl to thereby obtain culture fluid. This culture fluid contained 2.4% of the diol, 0.3% of sclareol, 96.5% of water, and 0.6% of other solids (bacterial cells and the like).

[Analysis Methods]

Sclareol, sclareolide and the dial were extracted from the culture fluid using ethyl acetate, and were appropriately diluted. An analysis by gas chromatography (GC) was performed to measure the contents. The GC analysis was performed with a 6890N GC System (manufactured by Agilent Technologies, Inc.), and the analysis conditions were as follows. An FID (Flame Ionization Detector) (manufactured by Agilent Technologies, Inc.) was used as a detector, the injection inlet temperature was set at 250° C., and the injection method was set in the split mode (split ratio 100:1). The total flow was 200 mL/min, the column flow rate was 0.4 mL/min, the column was DB-WAX ($\phi$0.1 mm×10 m) (manufactured by J&W Technology, Ltd.), and the oven temperature was 250° C.

The water contained in the culture fluid was calculated from the amount of weight loss after the culture fluid was dried for 2 hours using an electric dryer at 120° C.

[Method for Evaluation of Odor]

The odor evaluation of the crystals of the diol was performed by seven panels according to the criteria shown below, and the average value was designated as the odor evaluation value.

5: A strong odor of the microbial culture fluid remains.
4: A slightly strong odor of the microbial culture fluid remains.
3: The odor of the microbial culture fluid is weak.
2: The odor of the microbial culture fluid is negligible.
1: There is no odor of the microbial culture fluid.

[Method for Evaluation of Color of Extract Liquid]

For the evaluation of the color of the diol extract liquid, the microorganisms were removed from the extract liquid using a centrifuge (apparatus: HITACHI CR22GII, rotor: R9AF2, condition: 7420 r/min, 5 minutes), the absorbance of the resultant supernatant was measured at wavelength of 420 nm (apparatus: SHIMADZU UV-2450) and the dial concentration (g/L) was measured by GC analysis. Subsequently, the absorbance was divided by the dial concentration (g/L), and the smaller value indicates more satisfactory color tone.

[Method for Evaluation of Color of Crystals]

The color of crystals of the dial was measured using a color measurement colorimeter ZE-2000 type (manufactured by Nippon Denshoku Industries Co., Ltd.). As the value (b value) representing a yellowish tinge is smaller, the color tone is more satisfactory.

Example 1

To 500 mL of the culture fluid obtained in the [Microbial conversion] described above, 500 mL of toluene (SP value of 8.9) was added and mixed with each other for 15 minutes (temperature of the fluid, 25° C.) to dissolve the diol. By static separation for 30 minutes, the aqueous phase containing the microorganisms was removed. Subsequently, from the solvent phase obtained, the solvent was distilled away under reduced pressure at 60 to 80° C. to precipitate the diol. Thereafter, by drying at 70° C., crystals of the diol were obtained. The results are shown in the Table 1.

Comparative Example 1 and 2

Crystals of the diol were obtained in the same manner as the Example 1 except that toluene was replaced with ethyl acetate (SP value of 9.1) or hexane (SP value of 7.3). The results are shown in the Table 1.

Example 2

500 mL of the culture fluid obtained in the [Microbial conversion] described above was treated by using a cylinder type centrifuge (apparatus: HITACHI CR22GII) at 25° C. and acceleration speed of 3000 G for 5 minutes to obtain precipitates. Water content in the precipitates was 60% by weight. The precipitates of the culture fluid were added to 500 mL of toluene (SP value of 8.9) and mixed with each other for 15 minutes (temperature of the fluid, 25° C.) to dissolve the diol. Using the same centrifuge, it was treated at 25° C. and acceleration speed of 6000 G for 10 minutes to remove the aqueous phase containing the microorganisms. Subsequently, from the solvent phase obtained, the solvent was distilled away under reduced pressure at 60 to 80° C. to precipitate the diol. Thereafter, by drying at 70° C., crystals of the diol were obtained. The results are shown in the Table 1.

Example 3

To 500 mL of the culture fluid obtained in the [Microbial conversion] described above, 125 mL of toluene (SP value of 8.9) was added and mixed with each other for 15 minutes (temperature of the fluid, 60° C.) to dissolve the diol. By static separation for 30 minutes, the aqueous phase containing the microorganisms was removed. Subsequently, from the solvent phase obtained, the solvent was distilled awasy under reduced pressure at 60 to 80° C. to precipitate the diol. Thereafter, by drying at 70° C., crystals of the diol were obtained. The results are shown in the Table 1.

Example 4

Crystals of the diol were obtained in the same manner as the Example 1 except that toluene was replaced with 4-methyl-2-pentanone (SP value of 8.4). The results are shown in the Table 1.

TABLE 1

|  |  | Example 1 | Example 2 | Example 3 | Example 4 | Com. Example 1 | Com. Example 2 |
|---|---|---|---|---|---|---|---|
| Method | Method for pre-treatment of culture product | None | Centrifugation | None | None | None | None |

TABLE 1-continued

|  |  | Example 1 | Example 2 | Example 3 | Example 4 | Com. Example 1 | Com. Example 2 |
|---|---|---|---|---|---|---|---|
|  | Solvent used | Toluene | Toluene | Toluene | 4-Methyl-2-pentanone | Ethyl acetate | Hexane |
|  | SP value of solvent used | 8.9 | 8.9 | 8.9 | 8.4 | 9.1 | 7.3 |
|  | Use amount of solvent (per amount of culture fluid) | 100 vol % | 100 vol % | 25 vol % | 100 vol % | 100 vol % | 100 vol % |
|  | Temperature of mixture fluid | 25° C. | 25° C. | 60° C. | 25° C. | 25° C. | 25° C. |
| Evaluation | Recovery ratio of diol pre-treated | — | 98% | — | — | — | — |
|  | Recovery ratio of diol extracted | 85% | 100% | 86% | 73% | 96% | 3% |
|  | Total recovery ratio of diol | 85% | 98% | 86% | 73% | 96% | 3% |
|  | Color of extract liquid | 0.0001 | 0.0001 | 0.0002 | 0.0000 | 0.0010 | — |
|  | Color of crystals | 2.82 | 2.46 | 3.68 | 4.60 | 9.41 | — |
|  | Odor evaluation | 2 | 1 | 2 | 2 | 4 | — |

From the results of the Table 1, the diol obtained by mixing a culture fluid with a solvent having an SP value within the range of 7.5 to 9.0, removing an aqueous phase, and after that removing the solvent by distillation was found to be a product with very high quality exhibiting favorable color and reduced culture odor. On the other hand, the product obtained by using a solvent having an SP value outside the range of the present invention exhibited yellowish color and strong culture odor. Further, by removing a part of water before mixing with the solvent, more favorable color was obtained, the culture odor was further reduced, and moreover the yield of the diol was improved. According to the method of the present invention, the recovery ratio (yield) of the diol is 70% or more, showing sufficiently high efficiency for a production method.

The invention claimed is:

1. A method of obtaining purified 1-(2-hydroxyethyl)-2,5,5,8a-tetramethyldecahydronaphthalene-2-ol represented by the formula (2),

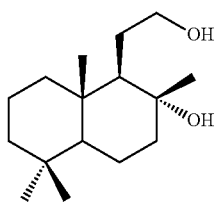

(2)

comprising the steps of:
carrying out microbial conversion using a compound(s) represented by the following formula (1a) and/or (1b) as a substrate to obtain a culture product,

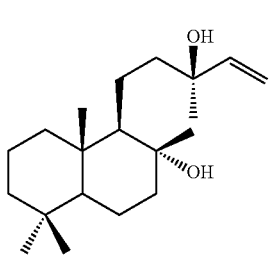

(1a)

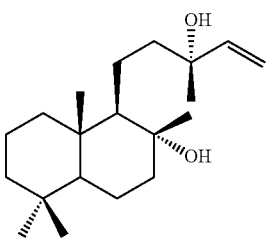

(1b)

mixing the culture product, in which microorganisms obtained by the microbial conversion are contained, and a solvent having an SP value within the range of 8.4 to 8.9 $[cal/cm^3]^{1/2}$ to obtain a mixture, and subsequently removing the aqueous phase from the mixture;

wherein any filtering step is not carried out before mixing the culture product and the solvent.

2. The production method according to claim 1, wherein the solvent is one or two or more kinds selected from cyclohexane, 4-methyl-2-pentanone, xylene, and toluene.

3. The production method according to claim 1, further comprising a step of lowering the water content in the culture product to 80% by weight or less before the culture product in which microorganisms is mixed with the solvent.

4. The production method according to claim 1, further comprising a step of removing a part of water contained in the culture product by centrifugation before the culture product in which microorganisms are contained is mixed with a solvent.

* * * * *